United States Patent [19]

Eichmiller

[11] Patent Number: 5,190,990
[45] Date of Patent: Mar. 2, 1993

[54] DEVICE AND METHOD FOR SHIELDING HEALTHY TISSUE DURING RADIATION THERAPY

[75] Inventor: Frederick Eichmiller, Ijamsville, Md.

[73] Assignee: American Dental Association Health Foundation, Gaithersburg, Md.

[21] Appl. No.: 515,827

[22] Filed: Apr. 27, 1990

[51] Int. Cl.$^5$ .............................................. G21K 1/10
[52] U.S. Cl. .................................... 523/137; 524/440; 524/441; 524/588; 250/515.1; 250/519.1; 128/862
[58] Field of Search ............... 523/137; 524/440, 441, 524/588; 250/515.1, 519.1; 128/862

[56] References Cited

U.S. PATENT DOCUMENTS

| | | | |
|---|---|---|---|
| 2,367,738 | 1/1945 | Robertson et al. | 523/137 |
| 3,723,481 | 3/1973 | Bobear | 524/441 |
| 4,011,360 | 3/1977 | Walsh | 524/434 |
| 4,461,865 | 7/1984 | Maeda et al. | 524/441 |
| 4,474,685 | 10/1984 | Annis | 524/441 |
| 4,533,685 | 8/1985 | Hudgin et al. | 524/440 |
| 4,695,404 | 9/1987 | Kwong | 523/137 |
| 4,699,743 | 10/1987 | Nakamura et al. | 524/588 |
| 4,963,291 | 10/1990 | Bercaw | 524/440 |

OTHER PUBLICATIONS

Bowen, R. L., "Effect of Particle Shape and Size Distribution in a Reinforced Polymer," *J. Amer. Dent. Assoc.* 69:481–495 (1964).

Johns, H. E., *The Physics of Radiology*, second edition (Springfield, Ill., Charles C. Thomas, 1961) p. 633.

Saylor, M. et al. "A Thin Film Recording Medium for Use in Food Irradiation," In: Proceedings, 6th International Meeting on Radiation Process, Ottawa, Can., 1987.

Ridder, R. W. et al., "Process Control During High Pressure Atomization," *Mat. Sci. and Eng.* 98:47–51 (1988).

Stanford, J. W. et al., "A Revision of American Dental Associations Specification No. 3 for Dental Impression Compound," *J. Amer. Dent. Assoc.* 56–64 (1955).

Phillips, T. H. et al., "Radiation Modalities in Treatment of Cancer of the Oral Cavity," *J. Prosthet, Dent.* 27:413–418 (1972).

Fernandez, V. C., et al., "Efficacy of Radiation Protection Prostheses in Controlling Radiation Induced Xerostomis," *J. Indian Dent. Assoc.* 56:371–378 (1984).

Toljanic, et al., "Radiation Therapy and Management of the Irradiated Patient," *J. Prosthet, Dent.* 52:852–857 (1984).

Beumer, J., et al., "Hard and Soft Tissue Necrosis Following Radiation Therapy for Oral Cancer," *J. Prosthet. Dent.* 27:640–644 (1972).

Larson, D. L., "Management of Complications of Radiotherapy of the Head and Neck," Surgical Clinics of North America, 66:169–182 (1986).

Beumer, J., et al., "Radiation Therapy of the Oral Cavity; Sequelae and Management", Part I, *Head and Neck Surgery*, 1:301–312 (1979).

Textbook of Radiotherapy, edited by G. H. Fletcher, second ed. (Philadelphis, Lea, and Febiger, 1973).

(List continued on next page.)

*Primary Examiner*—Melvyn I. Marquis
*Assistant Examiner*—Karen A. Hellender
*Attorney, Agent, or Firm*—Allegretti & Witcoff, Ltd.

[57] ABSTRACT

During radiotherapy for malignant conditions, healthy tissues can suffer from radiation damage. Traditional radiation shields designed to protect healthy tissues are prepared by a lengthy, multi-step complex procedure. Materials are described for preparation of a radiation shield for use during radiation therapy, especially therapy of the head and neck, where the material comprises a composite of non-radioactive, non-toxic high atomic density metal or metal alloy spherical particles dispersed in a manually moldable elastomeric material. Custom radiation shields are formulated of this material without the need for use of impressions or molds. Healthy tissues may then be shielded during radiation therapy by positioning the custom-fitted radiation shield in the desired location on the patient's body.

9 Claims, 3 Drawing Sheets

Radiation Therapy and Their Management," *Prosthet Dent.* 49:514–522 (1983).

Fleming, T. J. et al. (1983): "A Tongue Shielding Radiation Stent," *J. Prosthet, Dent.* 49:389–390.

McLaughlin, W. L., et al., "Sensitometry of a New Radiochromic Film Dosimeter Response to Gamma Radiation and Electron Beams," *Nuclear Instruments and Methods* (recent publication).

Poole, T. S. et al., "Use of Protective Prostheses During Radiation Therapy", *J. Amer. Dent. Assn.,* 112:485–488 (1986).

Dreizen S., et al., "Radiation-Induced Xerostomia in Cancer Patients, Effect on Salvary and Serum Electrolytes," *Cancer* 38:273–278 (1976).

Dreizen, S., et al., "Oral Complication of Cancer Radiotherapy," *Postgrad. Med.* 61:85–92 (1977); cited by I. L. Shannon, Management of Head and Neck Irradiated Patients, *Adv. Physiol Sci.,* vol. 28, Saliva and Salivation (1980).

Thambi, V., et al., Dose Perturbation from Gold Fillings in Patients with Head and Neck Cancers, *Int. J. Rad. Oncol. Biol. Physics* 5:581–582 (1979).

Benak, S. et al., "Treatment of Carcinoma of the Oral Cavity," *Radiology,* 96:137–143 (1970).

Engelmeier, R. et al., "Protecting the Tongue During Head and Neck Irradiation," *General Dent.* May–Jun. 1983 pp. 213–215.

Engelmeier, R. et al., "Complications of Head and Neck

DEVICE AND METHOD FOR SHIELDING HEALTHY TISSUE DURING RADIATION THERAPY

BACKGROUND OF THE INVENTION

This invention was supported in part by research grant number DE09322-01 to the American Dental Association Health Foundation from the National Institute of Dental Research.

This invention relates to the field of shielding healthy tissues from radiation damage during radiotherapy for malignant conditions. It also relates particularly to the field of such shielding where the tissues to be shielded are of irregular conformation and/or associated with metallic restorations or prostheses, as in the mouth.

Approximately 30,000 people were diagnosed with some form of oral cancer in 1985, accounting for more than 3% of all patients with cancer and 3% of cancer related deaths (American Cancer Society, 1985). Treatment of oral malignancies is a great challenge to radiotherapists because of their potential curability.

Treatment of head and neck tumors by electron, x-, or gamma-ray teletherapy is a well established and highly successful modality. S. Benak, F. Buschke, and M. Galanta, "Treatment of Carcinoma of the Oral Cavity," Radiology 96, 137–143 (1970), T. L. Phillips, and S. Benak, "Radiation Modalities in Treatment of Cancer of the Oral Cavity," J. Prosthet. Dent. 27, 413 (1972); J. A. Toljanic, and V. W. Saunders, "Radiation Therapy and Management of the Irradiated Patient," J. Prosthet. Dent. 52, 852 (1984). The ease of access, localization of malignancies, and relatively high responsiveness of these tumors to radiation leads to encouraging treatment prognoses.

One of the major complications of head and neck radiotherapy is the post-irradiation damage to healthy tissues in front of, adjacent to, or beyond the treated tumors. This latent radiation damage to nonmalignant tissues can range in severity from slight post-treatment discomfort to life-threatening necrosis. Manifestations of radiation damage include dry mouth (xerostomia), loss of taste, changes in oral microflora and salivary chemistry, erythema and ulceration of oral mucosa, glossitis and edema of the tongue, moniliasis of the lips, salivary gland dysfunction and edema, dysphagia, muscle fibrosis, and osteonecrosis. J. Beumer, S. Silverman, and S. B. Benak, "Hard and Soft Tissue Necrosis Following Radiation Therapy for Oral Cancer," J. Prosthet. Dent. 27:640–644 (1972); J. Beumer, T. R. Curtis, and R. Harrison, "Radiation Therapy of the Oral Cavity: Sequelae and Management," Part 1, Head and Neck Surgery, 1:301–312 (1979); D. L. Larson, "Management of Complications of Radiotherapy of the Head and Neck," Surgical Clinics of North America 66:169–182 (1986); S. Driezen, L. R. Brown, S. Handler, and B. M. Levy, "Radiation-Induced Xerostomia in Cancer Patients, Effect on Salivary and Serum Electrolytes," Cancer 38, 273–278 (1976); S. Driezen, T. E. Daly, J. B. Drane, and L. R. Brown, "Oral Complications of Cancer Radiotherapy," Postgrad. Med. 61, 85–92 (1977); cited by I. L. Shannon, "Management of Head and Neck Irradiated Patients," Adv. Physiol Sci. Vol. 28, Saliva and Salivation (1980). Diminished salivary function is a very common post-irradiation condition which often leads to accelerated tooth decay or "radiation caries". J. Beumer, S. Silverman, and S. B. Benak, "Hard and Soft Tissue Necroses Following Radiation Therapy for Oral Cancer," J. Prosthet. Dent. 27:640–644 (1972); J. Beumer, T. R. Curtis, and R. Harrison, "Radiation Therapy of the Oral Cavity: Sequelae and Management," Part 1, Head and Neck Surgery 1:301–408 (1979), C. Fernandez, S. Master, B. Sarosh, and M. Turner, "Efficacy of Radiation Protection Prosthesis in Controlling Radiation Induced Xerostomia," J. Indian Dent. Assoc. 56:371–378 (1984).

The severity of the above side effects on normal tissues has been reduced by a number of techniques including selection of the radiation source to have the least effect on normal surrounding or overlying tissues, careful positioning and collimation of the source beam, and shielding.

In treatment of head and neck lesions with high-intensity radiation (teletherapy), an important aspect of the protection of healthy tissues has thus been manufactured and application of an individually customized prosthetic appliance, which is designed, modelled, and formed into a custom-made metal on plastic shield. Specifically, in treating lesions of the skin or oral tissues with electrons, photons, x-, or gamma-rays, shields and stents containing cast forms made from metals or alloys of high atomic density elements have been used to protect surrounding tissues.

The fabrication of these appliances is a multi-step procedure often requiring the cooperative efforts of the radiotherapist and the dentist/prosthodontist. First, impressions are made of the intra- or extraoral treatment site and a plaster model of the tissues fabricated from these. A wax replica of the shielding prosthesis is fabricated on the plaster model and this is cast in polymerized acrylic by a lost-wax method to form the working stent. This stent is tried for fit and then hollowed out in the appropriate region for incorporation of a metal liner, which serves as the customized radiation shield. Molten lead or a low-temperature-melting alloy such as Lipowitz metal (50% bismuth, 26.7% lead, 3.3% tin, and 10% cadmium) is then poured and formed into the working polyacrylic stent, to form the shielding appliance, leaving a window exposing only the tissue being irradiated, where appropriate. After cooling, the metal casting is covered with an additional layer of polyacrylic. The completed appliance is then polished and adjusted to the final fit. Textbook of Radiotherapy, edited by G. H. Fletcher, second ed. (Philadelphia, Lea and Febiger, 1973).

SUMMARY OF THE INVENTION

The prior art method for shielding healthy tissues during high energy radiation therapy is slow and technique-intensive, and can add to patient discomfort and inconvenience during molding and fabrication of the shield. The difficulty encountered in fabricating a well-fitting stent particularly for head and neck cancer which can be comfortably worn during repeated treatments makes utilization of these techniques problematic for treatment facilities not having access to dental or maxillofacial services. The increasing utilization of outpatient clinics specializing in radiotherapy delivery enhances the need for shielding materials and techniques which can be much more easily fabricated and fitted in the treatment setting.

It is an object of the present invention to provide radiation shielding and absorbing materials that can be more easily fabricated and fitted in clinics specializing in radiotherapy. These materials will then reduce the frequency, severity and morbidity of side effects from treatment of malignant diseases.

It is an additional object of the present invention to provide protective prostheses which are of minimal weight, easy to adjust in the treatment room, easy to repair, easy to clean and easy to place and remove.

The invention contemplates a material for preparation of a radiation shield for use during radiation therapy, where the material comprises a composite of non-radioactive non-toxic high atomic density metal or metal alloy spherical particles dispersed in a manually moldable elastomeric material, which will harden within a clinically acceptable time period to a firm or set structure which is semi-rigid in that it is elastomeric, i.e., deformable, but returns to its original conformation, when the deforming force is removed. Within the purview of the invention are mixtures of Sn-Sb, Ag-Cu, Cu-Al, Au-Cu, Sn-Bi, Ag-Pd, and stainless steel alloy spherical particle powders in a polymerizable elastomeric precursor or resin such as vinyl polysiloxane resin or silicone resin. Also contemplated as part of the invention are custom radiation shields formulated of this material. A further aspect of the invention is a method for fabricating such a custom shield which comprises mixing a powder of non-radioactive non-toxic high atomic density metal or metal alloy spherical particles with a manually moldable elastomeric precursor to form a moldable composite, custom fitting the moldable composite to the patient's tissues which are to be shielded during radiation therapy, and permitting the composite to harden. The inventive method for shielding healthy tissues during radiation therapy further comprises positioning the custom-fitted hardened radiation shield in the desired location on the patient's body prior to and during radiation treatment.

It is a further aim of the present invention to provide an improved shielding stent material, device and method for intraoral and extraoral use in teletherapy. The inventive composite material is especially designed to allow for ease and speed of fabrication of shielding appliances. The material is formulated to be readily shaped to an individual anatomical form without excessive laboratory support, prosthetic expertise, or discomfort to the patient. Appliances can be fabricated from this material directly on the patient without the taking of preliminary impressions, heat-treating of acrylics, or casting of metals. The material can be formed and molded in the plastic state and chemically polymerized to form a firm elastomeric composite. This new material allows for much higher metallic loading fractions than are commonly used in filled resin formulations.

DESCRIPTION OF THE PREFERRED EMBODIMENTS

An important component of the radiation shields of the present invention is the powder of non-radioactive non-toxic high atomic density metal or metal alloy spherical particles. The high atomic density of the metal or metal alloy is desirable because it correlates with high Z (electron density within the atom). Heavy metals or alloys of heavy metals which can be atomized to very small spherical particles are particularly preferred.

The use of molten atomization processing of metals or metal alloys makes possible the formation of highly spherical powders of very small particle sizes of, e.g., 40 microns and less. In general, powders with average particle sizes of about 1 to about 100 $\mu$m are preferred, with 40 microns or smaller particularly preferred. Lathe cut or ground powders become stiff and unformable at high packing densities due to physical interferences on the particle surfaces. The use of spherical particles makes possible very dense packing without the loss of material flow properties.

The atomization process used for fabrication of the powder alloys is similar to techniques described by Ridder and Biancaniello (1988). This process uses high pressure inert gas atomization field kept under inert gas pressures in excess of 100 bar. The particle size and shape are controlled by the molten metal pressure at the nozzle, the metal flow rate, and the solidification field pressure. Particle sizes are determined by laser diffraction, which measures the forward scattering of laser light through the process powder-stream, and this information is used to control the atomization processing parameters. The particles are then separated and graded.

Examples of metal alloy compositions which may be used to formulate the spherical particle filler include 60 wt % Sn-40 wt % Sb; 70 wt % Ag-30 wt % Cu eutectic, 95 wt % Sn-5 wt % Sb, 81.5 wt % Cu-9.5 wt % Al and 72 wt % Ag-18 wt % Cu. These proportions of various metals are illustrative only, and the proportions may of course vary. Alloys of lead, bismuth, tin and cadmium are other choices. Metal powders of these and similar alloys with high packing densities are believed to be capable of exhibiting shielding qualities similar to solid metals when dispersed in an elastomeric precursor. Mixtures of particles of more than one composition type may be employed if desired.

The powder of spherical metal or metal alloy particles is then homogeneously mixed as a high concentration filler into the liquid component of pre-polymerized elastomeric resin which can be worked by hand or with hand tools and which is polymerizable to a semi-rigid state within a clinically acceptable time period. Very high volume fractions of these powders can be incorporated into a polymer matrix to form a moldable mass with high metal density.

Specifically, once the metal powder has been processed, it is blended in varying proportions with elastomeric polymers to form mixtures which can be easily handled and processed into prosthetic appliances. Packing density of the metal particles is controlled by gap-graded blending of different particle sizes as is common to the optimization of filler configuration in composite dental materials (Bowen, 1964). The filled metal-polymer blends are formulated to give the maximum stopping power with minimal effects from electron scatter while maintaining working consistencies adequate for convenient fabrication using both direct and indirect techniques.

The level of metal or metal alloy spherical particle filler present in the elastomeric resin is variable depending on the shielding requirements necessitated by the radiation therapy which is indicated. Preferably the filler level is at least about 50 weight %, and may be as much as about 95 weight %, of the composite.

The elastomeric material should also be non-toxic under its conditions of use. The preferred elastomeric resins are, due to their ready availability, commercial addition-reaction polymerizable silicone impression materials. Silicones and vinyl polysiloxane compositions are suitable, for example. The polysiloxane materials rely on catalyzed addition reactions to initiate polymerization, which gives the greatest amount of control over the working and handling times. Especially preferred are vinyl polysiloxane impression materials such as Reprosil TM, available from Caulk/Dentsply in a form such that two equal parts of base and catalyst are mixed together. Other examples of silicone and vinyl polysiloxane precursors which may be employed include Hydrosil TM (Caulk/Dentsply), Impergum TM (Premier), Extrude TM (Kerr), Express TM (3M), Cuttersil TM (Cutter), Absolute TM (Coe), Baysilex TM (Cutter) and Cinch-Vinyl TM (Parkell).

Reprosil TM (Caulk/Dentsply) is a polysiloxane impression material available in three fluid viscosities (light, medium, and heavy) as well as a thicker putty consistency. The base component and catalyst component are supplied separately and mixed in equal volumes to initiate polymerization. Different proportions of metal powder are optimal for different therapeutic modalities, and depending on the type and amount of filler employed, the preferred viscosity of polysiloxane may vary. The metal alloy powder is blended using hand or mechanical spatulation with all three viscosities of the elastomer to form equal metal-fraction catalyst and base components of each. Materials may be selected which demonstrate a fluid viscosity capable of reproducing the detail of a standard test pattern utilized for testing detail reproduction (ADA Specification No. 3) for dental impression compound (Stanford et al., 1955) or which have the viscosity closest to impression putty which can be mixed by hand kneading. Modifications in viscosity may be achieved as needed, for example by the further addition of (1) filler in the form of metal powder, (2) colloidal silica powder, and/or (3) finely ground polymerized elastomer. Other additives may also be incorporated in the composite so long as they do not negate its usefulness for its intended purpose. The various components of the material for formulation of the shield may be packaged in a convenient kit, for example, with a putty component of metal powder in base resin, a putty component of metal powder in catalyst, a component of unfilled resin, and a component of adhesive.

Once the metal powders of high atomic density are blended as fillers with elastomeric polymer precursors to yield materials that can be mixed and applied directly without the laboratory fabrication of molds or models, both extra-oral and intra-oral shielding appliances can be conveniently formulated. The appliances may be fabricated in a reasonable amount of time (e.g., less than 20 minutes) within the radiotherapy treatment setting without the assistance of dental laboratory support.

For example, unfilled impression putty material may be mixed and rolled out to form a sheet of approximately 0.5 mm thickness. This sheet of material can then be adapted to the body contours by hand manipulation and allowed to set. Airways are established and eye and nose protection provided as needed with cotton according to techniques commonly used in the taking of facial impressions. A thin layer of impression tray adhesive may be applied if necessary to the set material. The metal-filled elastomer is then mixed and applied over the unfilled elastomer. Viscosity adjustments may be necessary to formulate a material which can be controlled adequately during this application. After curing, the stent is removed and the radiation treatment window cut into the mask wherever appropriate. The shield is then positioned on the patient so as to correctly locate the treatment window and shield periphery, and radiation therapy is conducted in accordance with the usual treatment regimen.

An example of the fabrication of an intraoral appliance would be the mixing of a thick putty consistency of the filled composite material and directly introducing it into the treatment site using a dental impression tray or by hand finger molding. After polymerization the shield would be removed, shaped and trimmed with a knife, and additions and corrections made where necessary by the adding of additional filled composite. Regions of high backscatter could be attenuated by the addition of a thin layer of unfilled polymer. The completed appliance could be reused for the duration of treatment sessions and could benefit additionally as a positioning stent for beam targeting.

One problem associated with the use of metal shielding devices is the formation of electron scatter when using gamma and x-ray sources. This secondary radiation is comprised of low energy electrons and positrons which have a very short range of 1 to 2 mm in tissue. This effect is observed around dental protheses such as gold crowns. Acute reactions have occurred in tissues immediately adjacent when these restorations are in the beam path. (Thambi et al., 1979). This secondary radiation can easily be absorbed in materials of low density such as wax (Thambi et al., 1979; Fleming and Rambach, 1983) or impression materials. Intraoral stents employing metal must be coated with a sufficient thickness of polymer so as to laminate the beam-blocking metal between layers of scatter-absorbing acrylic (Fleming and Rambach, 1983). The inventive materials with high metal volume may also require the addition of a layer of unfilled polymer to absorb the metal-induced scatter. Unfilled polymer of similar consistency and handling properties could be easy laminated to the inventive materials to absorb surface scatter.

Tests using collimated gamma-ray beams from a $^{60}$Co teletherapy unit show that quickly formed composites made of a flexible resin with high concentrations of powdered spherical metal alloys provide effective custom-designed shielding, as well as diminished backscattered radiation to normal tissues. An example of a successful formulation is a mixture of 90% by weight AgCu alloy powder in a vinyl polysiloxane resin. This material is a moldable putty which upon polymerization forms a rigid elastomeric material that is capable of attenuating approximately 50% of a $^{60}$Co beam at a thickness of only 2 cm. Interleaved stacks of calibrated thin radiochromic film strips and soft-tissue-simulating plastic (polystyrene) layers gave a means of mapping three-dimensional profiles of dose distributions adjacent to the high-density shielding materials using a spectrophotometer equipped with a gel scanner.

EXAMPLES I AND II

A study was performed to document the degree of shielding afforded by different resin-metal combinations and the optimum thickness of coatings required to limit dose enhancement due to backscatter of secondary electrons.

A commercially available vinyl polysiloxane (referred to henceforth as "PVS") impression material (Reprosil TM, Caulk/Dentsply) mixed in two equal parts, base and catalyst, was used as the elastomeric binder in the formulation of the test material. Equal quantities by weight of base and catalyst components were separately mixed with constant weights of one of two powdered spherical metal alloys. The two alloys used were a 60/40 weight-ratio Sn-Sb and a 70/30 weight-ratio Ag-Cu eutectic, in the form of spherical alloy powders. The alloy powders each exhibited an average particle size of 30 m.

The filled base and catalyst were combined and mixed by hand kneading for approximately one minute (the consistency was putty-like and maintained its form during setting). The mixed mass was then immediately compacted into a long plastic cylinder, 1 cm in diameter, and allowed to cure for 5 minutes, into a solid rod. The total working time was about 2 minutes and the setting time approximately 5 minutes. Sample disks were then cut from this rod in lengths ranging from 0.5 to 10 cm.

In order to measure radiation absorbed doses in water, $D_{water}$ (equivalent to absorbed dose in soft tissue), a new thin-film dosimetry medium (called Gaf-Chromic TM) was used. M. Saylor, T. T. Tomargo, W. L. McLaughlin, H. M. Khan, D. F. Lewis, and R. D. Schenfele, "A Thin Film Recording Medium for Use in Foot Irradiation," In: *Proceedings*, 6th International Meeting on Radiation Processing, Ottawa, Canada, 1987, *Radiat. Phys. Chem.*; W. L. McLaughlin, Chen Yun-Dong, C. G. Soares, A. Miller, G. Van Dyk, and D. F. Lewis, "Sensitometry of a New Radiochromic Film Dosimeter Response to Gamma Radiation and Electron Beams," (submitted to Nuclear Instruments and Methods, 1989). This coated radiochromic film has a sensor coating thickness of 6 μm on a film base of 100 μm polyester plastic. The film changes from a colorless to a high-resolution blue image with two absorption polysiloxane peaks (~650 and ~600 nm) due to irradiation, without need for development of the image. The useful dose range is approximately 50 to 1,000 Gy (gray (Gy), where 1 Gy=1 Jkg$^{-1}$, and in terms of the older unit of absorbed dose, rad, 1 Gy=100 rad) for radiographic imaging and dosimetry when the spectrophotometer measures the radiation-induced increase in absorbance at 650 or 600 nm (near the major and minor absorption peaks, respectively) as a function of the dose. These functions $\Delta A_{650}$ or $\Delta A_{600}$ versus $D_{water}$, are nearly linear over this dose range. M. Saylor, T. T. Tomargo, W. L. McLaughlin, H. M. Khan, D. F. Lewis, and R. D. Schenfele, "A Thin Film Recording Medium for Use in Foot Irradiation," In: *Proceedings*, 6th International Meeting on Radiation Processing, Ottawa, Canada, 1987, *Radiat. Phys. Chem.*

A calibration curve for the GafChromic TM film was generated by recording the values of $\Delta A_{650}$ versus scanning distance across adjacent square pieces of the film irradiated to the indicated series of doses, using the scanning spectrophotometer set at 650-nm wavelength (slit image with dimensions 0.05 mm by 3 mm). The spectrophotometric readings were made with unirradiated film in the reference beam. Film strips of various lengths, depending on the lateral dimensions required, were mechanically transported lengthwise past the slit image using a gel scanning attachment and aligned so that the long dimension of the slit was perpendicular to the direction of the film motion. A continuous record of $A_{650}$ as a function of distance along the length of the film provided a record of the lateral dose distribution according to the calibration of $\Delta A_{650}$ versus $D_{water}$.

For the depth-dose profile study, the test materials were 1-cm-thick unfilled PVS polymer, 1-cm-thick polystyrene, 1-cm-thick 80% Sn-Sb alloy powder in PVS, and 1- and 2-cm thick 80% and 90% Ag-Cu alloy powder in PVS. One specimen was fabricated from 80% Ag-Cu alloy powder in PVS, cut to 0.8-cm length, and covered on one side with 0.2-cm-thick polymer (PVS only) to shield against the backscatter of secondary electrons. Each of these cylinders was sandwiched end-on between two stacks of calibrated Gaf-Chromic TM dosimeter films. All films were irradiated with the 6-m sensor coating facing toward the specimen cylinder ends on both sides. The gamma-ray beam axis was perpendicular to the surfaces of the stacked films. A $^{60}$Co source of gamma radiation (mean energy 1.25 MeV) was used for the irradiations (nominal dose 100 Gy). A square collimator supplied a gamma-ray beam that was several centimeters larger than the lateral dimensions of the phantom.

For the measurement of absorbed dose versus thickness of the shielding material on the forward scatter side, ten different thickness cylinders of 90% Ag-Cu alloy powder in PVS, ranging from 0.5 to 10 cm in length, were placed on the radiation source side of the upper dosimeter films. The 20×20 cm collimated gamma-ray beam axis was perpendicular to the surfaces of the dosimeter films. Intimate contact was maintained between the shielding material and the thin sensor films in plane-parallel geometry. The phantom assembly was exposed to the same source and dose used in the previously described experiment.

Each dosimeter film was read spectrophotometrically in terms of absorbed dose, to water or soft tissue, as a function of distance over the length of the film strip. Since the response characteristics, radiation penetration, and scattering properties of the detector-polymer laminates were approximately the same as those of biological tissues (e.g., compact bone and striated muscle), the resulting three-dimensional dose distributions simulated those in living tissues on both the forward- and backscattering sides of the shielding composites.

Figure 1:
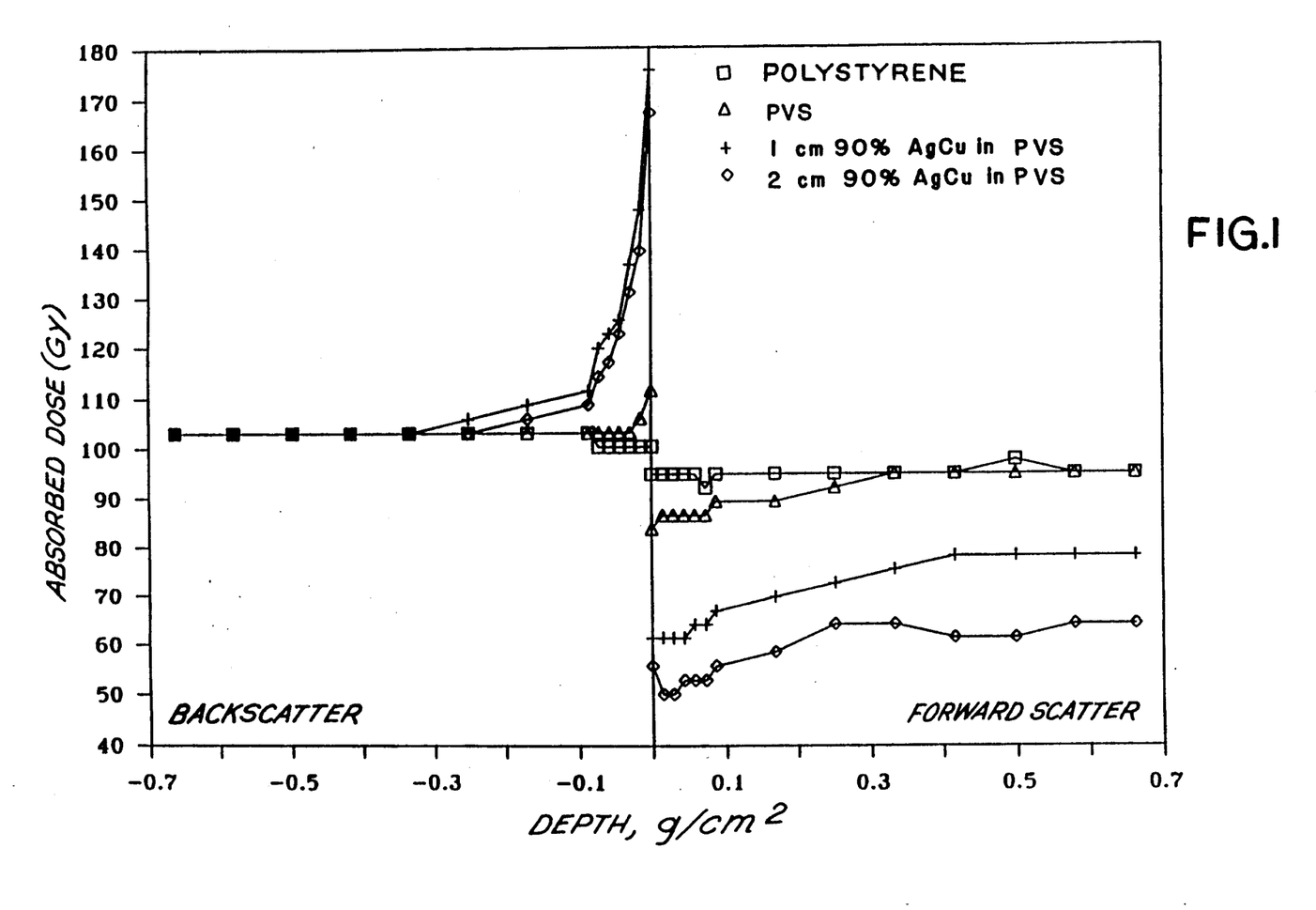
FIG. 1 is a graph of the $^{60}$Co gamma-ray depth-dose distributions on the forward-and backscatter sides of interfaces with four adjacent materials in the configuration as described in Examples I and II.

FIG. 1 shows the gamma-ray depth-dose distributions on forward- and backscatter sides of the test specimen-film interfaces, using four different test materials. Polystyrene spacers 0.5-cm thick, were interleaved between the eight most distant films on each side of the test materials to demonstrate the dose distributions as a function of depth in the plastic material away from the interface. Depth-dose distributions on both sides of the materials reached a plateau corresponding to conditions of electron equilibrium at a depth of approximately 0.3 g cm$^{-2}$ from the material interface. The "dose enhancement factor" (defined as the ratio of the maximum dose in water or soft tissue close to a high atomic-number interface material) on the backscattered side of the interface for each material was: 1.7 for 1-cm-thick 90% Ag-Cu powder in PVS, 1.6 for 2-cm-thick 90% Ag-Cu powder in PVS, 1.1 for 1-cm-thick PVS without metal filler, and 1.0 for 1-cm-thick polystyrene. Comparisons of the equilibrium dose levels on the backscatter and forward-scatter sides of the figure indicate the degree of attenuation of the $^{60}$Co beam by the samples.

Figure 2:
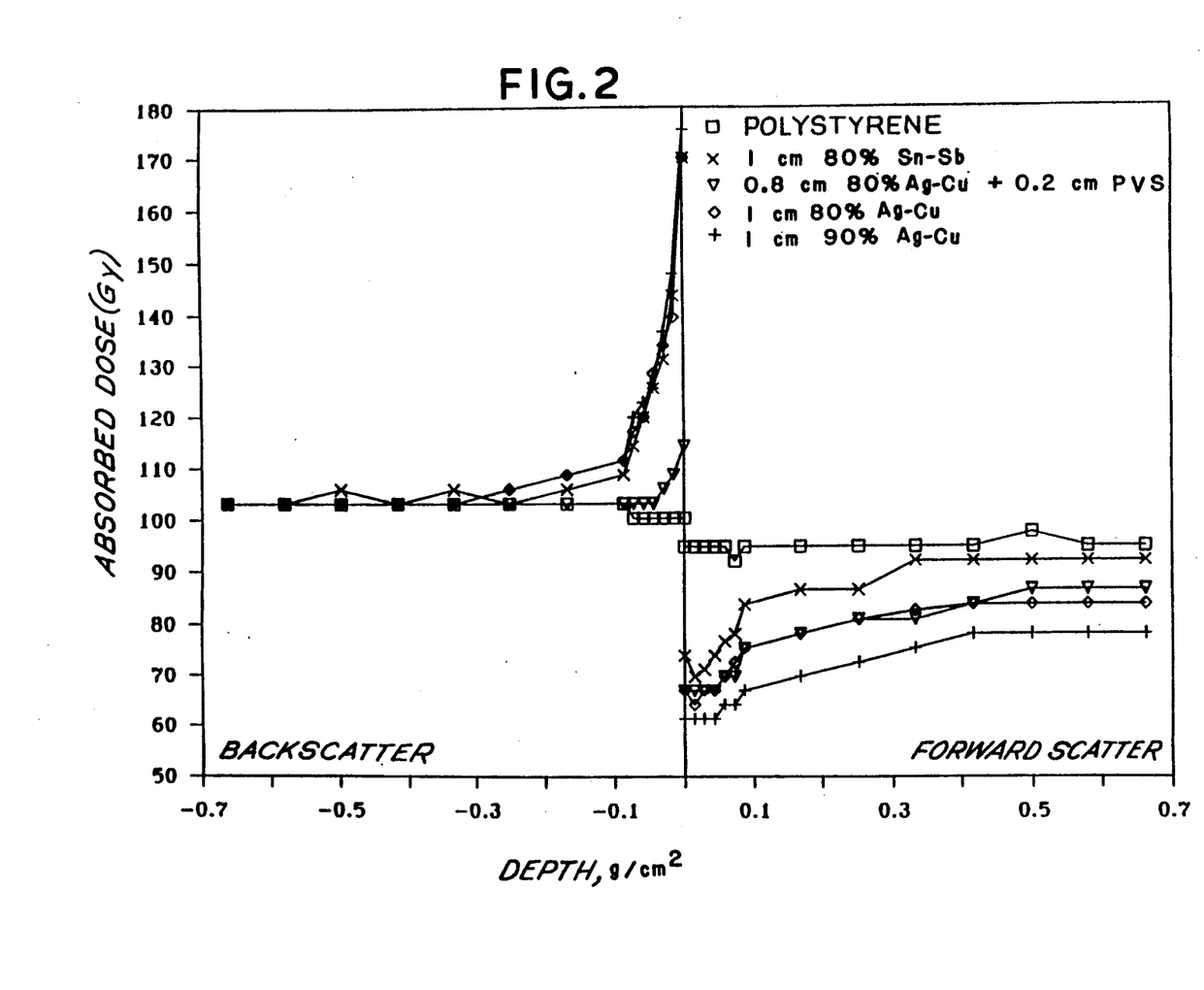
FIG. 2 is a graph of the $^{60}$Co gamma-ray depth-dose distributions on the forward-and backscatter sides of five materials in the configuration as described in Examples I and II.

FIG. 2 illustrates the forward- and backscatter depth-dose distributions at interfaces with 1 cm-thick polystyrene, 1-cm 80% Sn-Sb powder in PVS, 0.8-cm 80% Ag-Cu powder in PVS covered with 0.2-cm of unfilled PVS, 1-cm 80% Ag-Cu powder in PVS, and 1-cm-thick 90% Ag-Cu powder in PVS, when irradiated from one side by the gamma-ray beam to the total nominal dose of 100 Gy. The dose reached approximate equilibrium values for each material at distances greater than 0.3 g cm$^{-2}$, the range of the most penetrating secondary electrons. The dose enhancement factors on the backscattered side of the composite interfaces were: 1.6 for 1-cm 80% Sn-Sb and 1-cm-thick 90% Ag-Cu, 1.1 for 0.8-cm-thick 80% Ag-Cu covered with a 0.2-cm unfilled polymer layer, and 1.7 for 1-cm-thick 90% Ag-Cu. The reduction in backscatter with the sample containing the 0.2-cm layer of unfilled polymer is due to the attenuation of the low-energy electron scatter within this layer.

Figure 3:
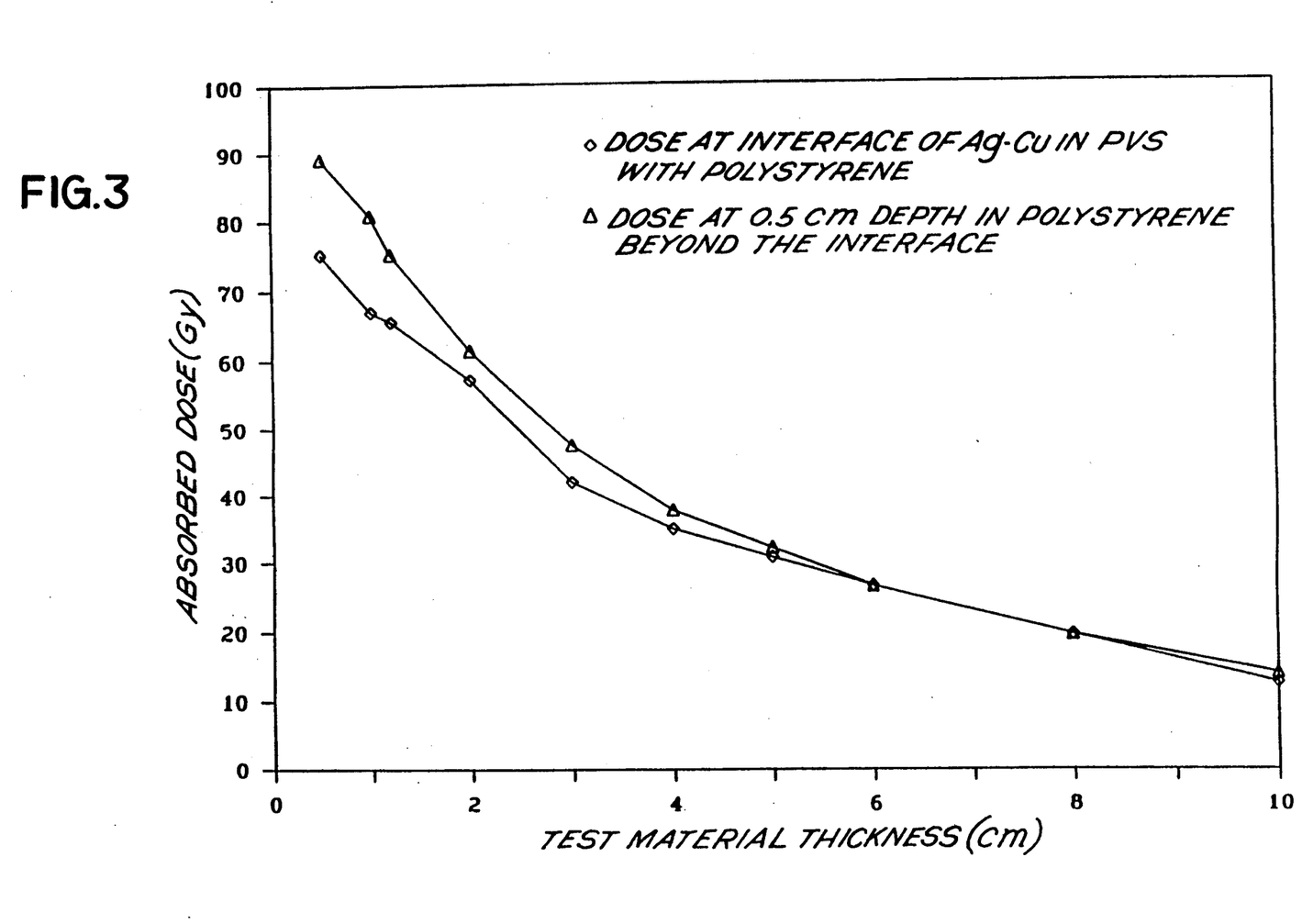
FIG. 3 is a graphical depiction of the effect of the shielding material thickness on transmitted dose in polystyrene adjacent to the interface with the test material (90% Ag-Cu in PVS). The two curves represent measurements on the forward-scatter side using a dosimeter film at the interface and a dosimeter film separated from the interface by 0.5 cm layer of polystyrene.

FIG. 3 illustrates the effect of shielding thickness in terms of the transmitted dose (Gy) versus thickness of 90% Ag-Cu powder in polysiloxane measured on the forward-scatter side of the composite shielding material. The reduction in transmitted dose is largely due to greater photon and secondary electron attenuation by the increasing thickness of denser absorbing materials. The half-dose thickness of this particular material was approximately 2 cm when exposed to $^{60}$Co gamma radiation.

In x- and γ-ray teletherapy, the forward- and backscattered doses in soft tissue adjacent to metallic or other high-density material exhibit a marked dose enhancement effect near the interface. This dose enhancement effect is much greater on the backscattering side of the interface and it increases with increasing density and atomic density of the scattering material. Forward scatter and attenuation contributions to the dose distributions are also dependent upon the distance from the interface and atomic density of interface material. In addition, the forward-scatter dose profile and degree of shielding vary with the thickness of the high atomic density interface material, due to greater photon attenuation by the thicker and denser absorbing materials. In general, the present experiments with $^{60}$Co gamma rays demonstrate that the "soft tissue" on the forward-scattering side of high atomic-number metal or metal-polymer composite is subjected to a significantly diminished radiation dose (as much as 50% lower) when the photon beam passes through the shielding layer containing Ag, Cu, Sn, Sb and polymer composites or combinations of these. A 90% Ag-Cu-PVS composite layer of 2-cm thickness provides shielding equivalent to approximately 1-cm of lead for $^{60}$Co gamma radiation, H. E. Johns, *The Physics of Radiology*, second edition (Springfield, Ill., Charles C. Thomas, 1961) p. 633, which is approximately one-half the dose that would be received without shielding. An important consideration to keep in mind is that the surface "soft tissues" would be overdosed by nearly a factor of two on the corresponding backscatter side, and therefore, the electron backscatter in the high atomic density prosthesis must be absorbed by a thin (2–3 mm) unfilled polymer layer.

Thus, these metal-polymer composites are effective shielding materials when used with $^{60}$Co radiation teletherapy.

EXAMPLE III

An experiment was run utilizing addition silicone impression materials to absorb radiation scatter only, with no attempt to shield surrounding tissues from incident (incoming) radiation around metallic restorations. This experiment was performed on a patient receiving 6000 rads of fractionated 6 MeV x-ray therapy for a tumor of the mandible where the lower left first molar was restored with silver-palladium crown and was directly in the beam path. A soft tissue lesion had appeared after 12 treatments in the 24 treatment regimen and therapy was interrupted to allow for healing. During the final 12 treatments a commercially available impression putty (Express TM, 3M) was mixed and formed into a quadrant bite block covering the metallic restoration and stabilizing the bite position. Dosimeters implanted into the impression material were used to measure dose directly adjacent to the teeth and 3 mm into the silicone material.

Direct dose measurements demonstrated a dose enhancement of over 20% adjacent to the crown and complete attenuation of the enhancement 3 mm into the shielding material. There was no recurrence of tissue damage in this case. Several patients were treated after this first trial using this technique, and none suffered this kind of soft tissue damage.

Thus, only a few millimeters of material of near-unit density are necessary to completely eliminate tissue damage due to localized scatter. Furthermore, this test demonstrated the convenience of using these autopolymerizing materials for this type of application. Fabrication of the shield required no laboratory support and was done in the radiotherapy treatment room in approximately ten minutes. The shielding stent was durable enough to be reused for the entire treatment regimen and was very amenable to utilization of the commonly used thermoluminescent detector (TLD) dosimetry. An added advantage was the stabilization of bite position allowing for more accurate and reproducible targeting of the treatment beam.

EXAMPLE IV

A spherically atomized powder of a tin-antimony (Sn-Sb) alloy was screened to grade the particle sizes to 40 micrometers and smaller. This powder was then blended individually into the base and catalyst components of a polysiloxane impression material (Reprosil TM, Caulk/Dentsply), which had a light-body consistency, to yield mixtures which were 80% by weight alloy. The use of the spherical powder resulted in a material which still had a fluid consistency and could be easily formed. The base and catalyst mixtures were combined and formed into blocks of material which were later cut to specified thicknesses. Setting time was within normal limits for the impression material, and the final polymer exhibited elastic properties similar to original impression material. One-centimeter cubes were cut from the cured metal-filled polymer using a diamond wafering saw (Isomet TM), and similar cubes were cut from a sample of the unfilled impression material. A phantom was assembled utilizing the two kinds of samples and a control of polystyrene; dosimetry films were stacked on both sides of the materials to measure the depth-dose profile around them.

The phantom was irradiated with 10 Gy (10,000 rad) of cobalt 60 gamma radiation and films were read on a scanning spectrophotometer. The resulting depth-dose profile indicated a surface backscatter similar to that experienced with metal interfaces. This indicates that the density of metal within the polymer was high enough to require an additional layer of low density polymer on the surface to absorb this short-range scatter. The total attenuated dose at the surface (primary beam plus secondary electrons) on the forward side of the Sn-Sb-filled material was approximately 70% of the polystyrene control dose and 80% of the dose level within the unfilled impression material. This represents a significant dose reduction considering the high energy of the 1.2 MeV cobalt beam which would normally be attenuated only 42% with 1 cm of the Lipowitz solid shielding alloy (Poole and Flaxman, 1986).

It should be understood that the foregoing disclosure emphasizes certain specific embodiments of the invention and that all modifications or alternatives equivalent thereto are within the spirit or scope of the invention as set forth in the appended claims.

I claim:

1. A method for shielding healthy tissues during radiation therapy which comprises covering those tissues during therapy with a radiation shield for use during high energy radiation therapy which is custom fitted to the conformation of tissue at the site of intended use, comprising the polymerized form of a composite of a manually moldable elastomeric material and a filler powder of spherical particles of non-toxic, non-radioactive high atomic density metal or metal alloys.

2. A method as in claim 1, wherein the elastomeric material is an addition-reaction polymerizable silicone impression material.

3. A method as in claim 1, wherein the elastomeric material is a silicone or vinyl polysiloxane composition.

4. A method as in claim 1, wherein the spherical particles of metal or metal alloy are of an average diameter between about 1 $\mu$m and about 100 $\mu$m.

5. A method as in claim 1, wherein the spherical particles of metal or metal alloy of of an average diameter less than 40 $\mu$m.

6. A method as in claim 1, wherein the spherical particles of metal or metal alloy are made by atomization.

7. A method as in claim 1, wherein the spherical particles of metal or metal alloy are selected from the group consisting of Sn-Sb, Ag-Cu, Cu-Al, Au-Cu, Sn-Bi, and Ag-Pd.

8. A method as in claim 1, wherein the spherical powder of metal or metal alloy constitutes between about 50 and about 95 weight percent of the composite.

9. A method for shielding healthy tissues during radiation therapy which comprises covering those tissues during therapy with a radiation shield prepared by a method comprising mixing a powder of non-toxic, non-radioactive high atomic density metal or metal alloy spherical particles with a precursor for a manually moldable polymerizable elastomeric material to form a composite, shaping the composite with manual pressure into the appropriate configuration to shield the healthy tissues of a patient surrounding an area to be subjected to radiation therapy, and polymerizing the elastomeric material.

* * * * *